United States Patent
Heath et al.

(10) Patent No.: US 8,647,633 B2
(45) Date of Patent: *Feb. 11, 2014

(54) RECOMBINANT F1-V PLAGUE VACCINE

(75) Inventors: David G. Heath, Lanstuhl (DE); Arthur M. Friedlander, Gaithersburg, MD (US); George W. Anderson, Jr., Frederick, MD (US); Susan L. Welkos, Frederick, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 1042 days.

This patent is subject to a terminal disclaimer.

(21) Appl. No.: 12/115,870

(22) Filed: May 6, 2008

(65) Prior Publication Data

US 2009/0022756 A1    Jan. 22, 2009

Related U.S. Application Data

(60) Continuation of application No. 10/752,951, filed on Jan. 7, 2004, which is a division of application No. 08/699,716, filed on Aug. 27, 1996.

(51) Int. Cl.
*A61K 39/00* (2006.01)

(52) U.S. Cl.
USPC ............................ 424/192.1; 424/190.1

(58) Field of Classification Search
None
See application file for complete search history.

(56) References Cited

FOREIGN PATENT DOCUMENTS

| WO | 95/17211 | * | 6/1995 |
|---|---|---|---|
| WO | 95/18231 | * | 7/1995 |

OTHER PUBLICATIONS

Clements (Infection and Immunity, 59(5):1159-1166, May 1990).*
Williamson et al (FEMS Immunology and Medical Microbiology 12:223-230, Dec. 1995).*
Leary et al. Infection and Immunity 63(8): 2854-58 8/95, publicly available as of Jul. 25, 1997).*
Motin et al, Infection and Immunity, 62(10):4192-4210, Oct. 1994.*
Marian Dorr, presentation Aug. 9, 1996.*
Greenspan et al. (Nature Biotechnology 7: 936-937, 1999).*
Greenbaum et al, Journal of Molecular Recognition, 20(2):75-82, 2007.*
Blythe et al, Protein Science 14:246-248, 2005.*

* cited by examiner

*Primary Examiner* — Patricia A Duffy
(74) *Attorney, Agent, or Firm* — Elizabeth Arwine

(57) ABSTRACT

Disclosed herein is a composition comprising a purified fusion protein comprising all or part of F1 antigen of *Yersinia pestis* fused to the amino terminus of all of V antigen of *Yersinia pestis, Yersinia enterocolitica*, or *Yersinia pseudotuberculosis* that is isolated from its expression vector.

9 Claims, 1 Drawing Sheet

RECOMBINANT F1-V PLAGUE VACCINE

CROSS REFERENCE TO RELATED APPLICATIONS

This application is a continuation of U.S. patent application Ser. No. 10/752,951, filed 7 Jan. 2004, which is a divisional of U.S. patent application Ser. No. 08/699,716, filed 27 Aug. 1996, both of which are herein incorporated by reference in their entirety.

INTRODUCTION

*Yersinia pestis* is the causative organism of plague in a wide range of animals including man. Bubonic plague in man is most commonly acquired from the bite of an infected flea and is characterized by the swelling of local lymph nodes which form buboes. One of the complications of bubonic plague is secondary pneumonia, and in these cases plague can be transmitted between humans by airborne droplets. Pneumonic plague, particularly, is extremely virulent and results in high mortality rates.

Plague is endemic in regions of North and South America, Africa, China and Asia and, as evidenced by the recent outbreak of pneumonic plague in India [Centers for Disease Control. (1994). Update: Human Plague—India. *MMWR* 43:722-723], epidemics of enormous consequences remain a potential for this organism. Thus, there is a clear need for a vaccine which would protect individuals living and traveling in endemic areas.

The current human, licensed, vaccines available for prevention of plague are whole cell vaccines. A number of formulations exist. The plague USP vaccine, comprising formaldehyde killed *Y. pestis* bacilli, which is administered to the body via intramuscular injection, produces local and systemic side-effects, ranging from mild headaches to severe malaise and fever. Additionally, the vaccine does not provide complete immunity, since vaccinated individuals can contract pneumonic plague, indicating inadequate immunity at mucosal surfaces.

The live attenuated vaccine EV76 [Meyer et al. (1974) *J. Infect. Dis.* 129 suppl., 13-18] was tested extensively and used in the former Soviet Union from 1939, although its efficacy in evoking an immune response in man is questionable [Meyer et al. (1974) *J. Infect. Dis.* 129 suppl., 85-120]. The virulence of EV76 differs in several animal species, and non-human primates are particularly susceptible to a chronic infection with this strain. In the Western World, the vaccine is considered to be unsuitable for mass vaccination due to the severity of the side-effects and the possibility of the strain reverting to full virulence.

Efforts to develop a more effective vaccine have focused on acellular subunits from *Y. pestis* as immunogens. Two of the candidate subunits are the F1 and V antigens. The capsule surrounding *Y. pestis* cells is composed of a protein component known as Fraction 1 (F1) [Baker et al. (1952) *J. Immunol.* 68: 131-145] which is only fully expressed at 37° C. and encoded on the 100 kb pFra plasmid [Protsenko et al. (1983) *Genetika* 19: 1081-1090]. This complex confers resistance to phagocytosis. Detection of antibodies to F1 is the basis of standard serological tests for the surveillance and diagnosis of plague as infected animals and humans produce a strong humoral response to the antigen [Shepherd et al. (1986) *J. Clin. Microbiol.* 24: 1075-1078; Williams et al. (1982) *Bull. World Health Organ.* 64: 745-752].

V antigen, postulated to act as a virulence factor, is a 37 kDa secreted protein which acts as a cytoplasmic regulator of Yops (*Yersinia* outer membrane protein) expression. The V antigen is encoded on a homologous 75 kb low-calcium response (LCR) plasmid present in *Y. pestis, Y. pseudotuberculosis* and *Y. enterocolitica*. This plasmid mediates the growth restriction of the organism observed in vitro at 37° C. in the presence of less than 2.5 mM $Ca^{2+}$. Under such conditions the cells fail to synthesize bulk vegetative proteins although a series of stress proteins and virulence factors are expressed. The V antigen provides both active and passive immunity against experimental infection with $F1^+$ strains [Lawton et al. (1963) *J. Immunol.* 91: 179-184; Leary et al. (1995) *Infect. Immun.* 63: 2854-2858; Nakajima et al. (1995) *Infect. Immun.* 63: 3021-3029].

Vaccines which have focused on the capsule protein, F1, expressed either as the purified protein [Baker et al. (1952) *J. Immunol.* 68: 131-145; Simpson et al. (1990) *Am. J. Trop. Med. Hyg.* 43: 389-396] or in aroA mutant of *Salmonella typhimurium* [Oyston et al. (1995) *Infect. Immun.* 63:563-568] protected mice against virulent *Y. pestis*. However, *Y. pestis* strains lacking or deficient in F1 were isolated from immunized animals after challenge with $F1^+$ organisms from wild rodents [Welkos et al. (1995) *Contrib. Microbiol. Immunol.* 13:299-305] and from a fatal human case of plague [Winter et al. (1960) *Bull. WHO* 23: 408-409]. Most importantly, $F1^-$ strains are virulent in mice [Worsham et al. (1995) *Contrib. Microbiol. Immunol.* 13: 325-327] and nonhuman primates [Friedlander et al. (1995) *Clin. Infect. Dis.* 21: (Suppl 2), S178-181] and we found in the present study that the human plague vaccine does not protect against infection with $F1^-$ organisms. This implies that, as originally suggested by Burrows [Burrows, T. W. (1957) *Nature* 179: 1246-1247], an improved plague vaccine protective against both $F1^-$ and $F1^+$ strains of *Y. pestis* must not rely solely on F1.

Therefore, there is a need to develop an improved vaccine protective against both $F1^-$ and $F1^+$ strains of *Y. pestis* suitable for human administration.

SUMMARY

The present invention is directed to a vaccine that satisfies this need. The vaccine of the present invention is protective against both $F1^-$ and $F1^+$ strains of *Y. pestis*. The vaccine of the present invention is composed of a fusion between a portion of the F1 protein and another protective immunogen, the V antigen. This invention is novel because it is a single constructed protein, F1-V, composed of two unique proteins, the entire F1 capsule antigen and V antigen. It induces an immunological response against both F1 protein and V antigen.

The invention was designed to be used in a vaccine affording protection against plague, and to solve the problem of protecting humans against both bubonic and pneumonic plague caused by infection by the subcutaneous (insect bite) and aerosol routes, respectively, with $F1^+$ or $F1^-$ plague organisms, or with strains which may vary in their V antigen.

The advantages of using this protein over the present whole cell vaccine are as follows:

The current licensed vaccine does not protect mice against subcutaneous challenge with $F1^-$ strains of *Y. pestis*, which have been shown to cause fatal disease in both humans and experimental animals infected by a peripheral, non-respiratory route. The new F1-V vaccine does protect mice against bubonic plague caused by subcutaneous challenge (insect bite) with $F1^-$ organisms.

The current licensed vaccine does not protect mice against pneumonic plague induced by aerosol challenge with $F1^-$ strains of *Y. pestis*. The new F1-V vaccine does protect mice against pneumonic plague caused by aerosol challenge with F1⁻ strains.

The current licensed vaccine does not protect mice against pneumonic plague when challenged by the respiratory route with F1⁺ strains of *Y. pestis*. The new F1-V vaccine does protect mice against pneumonic plague caused by aerosol challenge with F1⁺ strains.

The new F1-V vaccine is expected to protect humans against pneumonic plague produced by strains of *Y. pestis*, either naturally occurring or genetically engineered, which may be altered in their content or composition of V antigen, but which still contain F1. This is because the F1-V vaccine also contains F1. The current licensed vaccine does not protect against pneumonic plague induced by either F1⁻ or F1⁺ organisms when given by the aerosol route.

The new F1-V vaccine is composed of two antigens, both of which have been shown to be protective. The combination of both antigens should provide better protection against F1⁺ strains than either F1 or V when used alone as vaccines. This is possible because the immunity induced by F1 and by V occur by different mechanisms which may be additive or synergistic.

Approximately 8% of humans immunized with the current licensed human plague vaccine fail to develop an immune response to F1 [Marshall et al. (1974) *J. Inf. Dis.* 129:S26-S29]. These non-responders may well be at risk for development of plague. The inclusion of two different protective antigens in the same vaccine will help to eliminate the problem of non-responders to either of the individual antigens and so increase the overall efficacy of vaccination in a human population.

The new F1-V vaccine is composed of highly purified recombinant proteins which are very well defined. This contrasts with the present human licensed vaccine composed of whole bacteria. The nature of the protective immunogen(s) in the present licensed vaccine is completely unknown. The present licensed vaccine is known to contain and induce antibodies to F1 but it does not induce antibodies to V antigen in mice, suggesting that V antigen is absent.

The F1-V protein was constructed so that a single protein could be purified as a vaccine component rather than having to produce and purify F1 and V antigen separately. The purification of a single protein as opposed to two separate proteins could result in considerable savings when manufacturing a vaccine.

Therefore, it is an object of the present invention to provide a *Y. pestis* DNA fragment encoding 1563 bp of a fusion protein comprising the F1 protein fused at its carboxyl terminus to the amino terminus of the entire V antigen useful in the production of a diagnostic agent and a vaccine.

It is another object of the present invention to provide an amino acid sequence for *Y. pestis* F1-V protein encoding 521 amino acids.

It is another object of the invention to provide a recombinant vector comprising a vector and the above described DNA fragment for use as a DNA vaccine.

It is a further object of the present invention to provide a host cell transformed with any of the above-described recombinant DNA constructs for use as a live bacterial vaccine when the host cell is a bacteria such as Salmonella, BCG, or a live viral vaccine when the host cell is a virus such as adenovirus, or Venezuelan Equine Encephalitis virus. These transformed cells, bacteria and viruses can also be used as a source for the *Y. pestis* F1-V protein.

It is another object of the present invention to provide a method for producing *Y. pestis* F1-V fusion protein which comprises culturing a host cell under conditions such that a recombinant vector comprising a vector and the *Y. pestis* F1-V protein DNA fragment is expressed and F1-V protein is thereby produced, and isolating F1-V protein for use as a vaccine or a diagnostic agent.

It is still another object of the invention to provide a purified *Y. pestis* F1-V protein useful as a vaccine and a diagnostic agent.

It is a further object of the present invention to provide an antibody to the above-described F1-V protein for use as a therapeutic agent and a diagnostic agent.

It is yet another object of the invention to provide a *Y. pestis* vaccine comprising a F1-V protein effective for eliciting an antigenic and immunogenic response resulting in the protection of a mammal against *Y. pestis* infection by subcutaneous and aerosol route.

It is yet another object of the present invention to provide a method for the diagnosis of *Y. pestis* infection comprising the steps of:

(i) contacting a sample from an individual suspected of having the infection with antibodies which recognize F1-V protein; and (ii) detecting the presence or absence of a complex formed between *Y. pestis* F1 and/or V antigen and antibodies specific therefor.

It is a further object of the present invention to provide a diagnostic kit comprising a F1-V protein antibody and ancillary reagents suitable for use in detecting the presence *Y. pestis* in mammalian sputum, serum, or tissues.

It is yet another object of the present invention to provide a therapeutic method for the treatment or amelioration of symptoms of infection by *Y. pestis* and other species of *Yersinia* such as *Y. enterocolitica* and *Y. pseudotuberculosis*, said method comprising providing to an individual in need of such treatment an effective amount of sera from individuals immunized with F1-V protein in a pharmaceutically acceptable excipient.

It is further another object of the present invention to provide a therapeutic method for the treatment or amelioration of symptoms of *Yersinia* infection, said method comprising providing to an individual in need of such treatment an effective amount of antibodies against F1-V protein of *Yersinia pestis* and all or a portion of V antigen of *Yersinia enterocolitica* and *Yersinia pseudotuberculosis* in a pharmaceutically acceptable excipient.

It is still another object of the present invention to provide antigenic epitopes of F1-V protein, which are useful in peptide vaccine design.

BRIEF DESCRIPTION OF THE DRAWINGS

These and other features, aspects, and advantages of the present invention will become better understood with reference to the following description and appended claims, and accompanying drawings where:

DESCRIPTION

Figure 1:
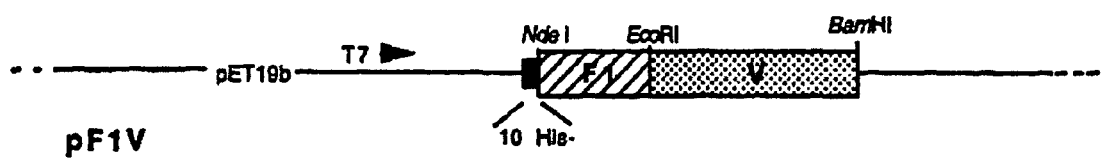
FIG. 1 shows plasmid pF1V showing an in-frame insertion of the F1 and V open reading frames at the NdeI and BamHI sites of pET19b separated by an inframe EcoRI site. F1-V was transcribed by using the T7 promoter (arrow) within pET19b after induction of T7 polymerase by isopropyl-β-D-thiogalactopyranoside (IPTG). The F1-V amino acid sequence begins with a His-Tag and enterokinase cleavage site derived from pET19b before the methionine start codon of F1. The F1 portion consists of 170 amino acids followed by two amino acids, asparagine and glutamine (encoded by the EcoRI site) and the entire sequence of the V antigen. F1-V, therefore, has 521 amino acids with a predicted molecular mass of 57,926 daltons.

In one embodiment, the present invention relates to a DNA or cDNA segment which encodes *Y. pestis* recombinant F1-V protein consisting of the F1 protein fused at its carboxyl terminus to the amino terminus of the entire V antigen. The sequence of the 1563 nucleotide DNA segment is specified in SEQ ID NO: 1.

DNA or polynucleotide sequences to which the invention also relates include fragments of F1 or V containing protective epitopes [Motin et al. (1994) *Infect Immun.* 62:4192-4201].

The derived polynucleotide is not necessarily physically derived from the nucleotide sequence shown in SEQ ID NO:1, but may be generated in any manner, including for example, chemical synthesis or DNA replication or reverse transcription or transcription, which are based on the information provided by the sequence of bases in the region(s) from which the polynucleotide is derived. In addition, combinations of regions corresponding to that of the designated sequence may be modified in ways known in the art to be consistent with an intended use. The sequences of the present invention can be used in diagnostic assays such as hybridization assays and polymerase chain reaction assays for the detection of F1 or V sequences of *Y. pestis*.

In another embodiment, the present invention relates to a recombinant DNA molecule that includes a vector and a DNA sequence as described above. The vector can take the form of a plasmid such as pET19b, pMBac/pPBac, pSSV1 or any broad host range expression vector such as viral vectors such as adenovirus or Venezuelan Equine Encephalitis virus and others known in the art.

In a further embodiment, the present invention relates to host cells stably transformed or transfected with the above-described recombinant DNA constructs. The host cell can be prokaryotic such as *Bacillus* or *E. coli*, or eukaryotic such as *Saccharomyces* or *Pichia*, or mammalian cells or insect cells. The vector containing the F1-V protein sequence is expressed in the bacteria and the expressed product used for diagnostic procedures or as a vaccine. Please see e.g., Maniatis, Fitsch and Sambrook, *Molecular Cloning: A Laboratory Manual* (1982) or *DNA Cloning*, Volumes I and II (D. N. Glover ed. 1985) for general cloning methods. The DNA sequence can be present in the vector operably linked to a highly purified IgG molecule, an adjuvant, a carrier, or an agent for aid in purification of F1-V protein. The transformed or transfected host cells can be used as a source of DNA sequences described above. When the recombinant molecule takes the form of an expression system, the transformed or transfected cells can be used as a source of the protein described below.

In another embodiment, the present invention relates to a DNA sequence incorporated into a vector which can be used as a DNA vaccine in animals, including humans, or which can be used in a live bacterial or viral vaccine, e.g. *Salmonella*, BCG, adenovirus, or Venezuelan Equine Encephalitis virus.

In another embodiment, the present invention relates to a *Y. pestis* F1-V fusion protein having an amino acid sequence corresponding to SEQ ID NO: 2 and encompassing 521 amino acids or any allelic variation thereof.

A polypeptide or amino acid sequence derived from the amino acid sequence in SEQ ID NO:2, refers to a polypeptide having an amino acid sequence identical to that of a polypeptide encoded in the sequence, or a portion thereof wherein the portion consists of at least 2-5 amino acids, and more preferably at least 8-10 amino acids, and even more preferably at least 11-15 amino acids, or which is immunologically identifiable with a polypeptide encoded in the sequence. The present invention relates to a F1-V protein where the F1 is fused by its carboxy-terminus to the amino-terminus of V antigen constructed with a polyhistidine and enterokinase site and where the F1 signal sequence is present Also embodied in this invention is a F1-V protein wherein the F1 is fused to the amino terminus of V, with or without any of the polyhistidine, enterokinase sites and the F1 signal sequence. In addition, a linker of additional amino acids can be fused in frame between the F1 and V antigen (or V antigen and F1) sequences or fragments thereof for convenience as long as the changes do not affect the immunological activity of the fusion protein.

A recombinant or derived polypeptide is not necessarily translated from a designated nucleic acid sequence, or the sequence in SEQ ID NO:1; it may be generated in any manner, including for example, chemical synthesis, or expression of a recombinant expression system. In addition the polypeptide can be fused to other proteins or polypeptides for the purposes of transport or for secretion from the cell or for increasing the protective efficacy in a vaccine. Some examples include the *Yersinia* outer proteins (Yops) of *Yersinia* species or fragments thereof, or the amino-terminal protective antigen binding domain of anthrax toxin lethal and edema factors to name a few.

In a further embodiment, the present invention relates to a method of producing F1-V protein which includes culturing the above-described host cells, under conditions such that the DNA fragment is expressed and F1-V is produced. F1-V can then be isolated using methodology well known in the art or by the production method described below. F1-V protein can be used as a vaccine for immunity against infection with the *Y. pestis* or as a diagnostic tool for detection of *Y. pestis* infection. The transformed host cells can be used to analyze the effectiveness of drugs and agents which inhibit *Y. pestis*, such as host proteins or chemically derived agents or other proteins which may interact with the bacteria to down-regulate or alter the expression of F1 protein or V antigen.

In another embodiment, the present invention relates to antibodies specific for the above-described F1-V protein. For instance, an antibody can be raised against the complete F1-V or against a portion thereof. Persons with ordinary skill in the art using standard methodology can raise monoclonal and polyclonal antibodies to F1-V of the present invention, or a unique portion thereof. Material and methods for producing antibodies are well known in the art (see for example Goding, in, *Monoclonal Antibodies: Principles and Practice*, Chapter 4, 1986). In addition, the protein or polypeptide can be fused to or combined with other proteins or polypeptides or adjuvants which increase its antigenicity, thereby producing higher titers of neutralizing antibody when used as a vaccine. Examples of such proteins or polypeptides include cholera toxin B subunit and any adjuvants or carriers safe for human use, such as aluminum hydroxide.

In a further embodiment, the present invention relates to a method of detecting the presence of *Y. pestis* infection or antibodies against *Y. pestis* in a sample. Using standard methodology well known in the art, a diagnostic assay can be constructed by coating on a surface (i.e. a solid support) for example, a microtitration plate or a membrane (e.g. nitrocellulose membrane), all or a unique portion of the F1-V protein described above, and contacting it with the serum of a person suspected of having plague. The presence of a resulting complex formed between F1-V protein and antibodies specific for either F1 or V in the serum can be detected by any of the known methods common in the art, such as fluorescent antibody spectroscopy or colorimetry. This method of detection can be used, for example, for the diagnosis of bubonic and pneumonic plague.

Similarly, antibodies to F1-V protein can be used in a rapid diagnostic assay to detect the presence of F1 and/or V antigen in the serum of patients infected with *Yersinia pestis*. Such a test may also be of value in the rapid diagnosis of infection in humans or animals with other *Yersinia* species by detection of V antigen in serum or tissue samples.

The ability of an individual to fight *Y. pestis* infection is dependent on the individual's ability to produce antibodies against *Y. pestis*. Diagnostic assays, similar to those described above, designed to measure the production of protective antibodies against F1-V can be used to measure an individual's response to receiving a plague vaccine.

In another embodiment, the present invention relates to a diagnostic kit which contains F1-V protein from *Y. pestis* and ancillary reagents that are suitable for use in detecting the presence of antibodies to *Y. pestis, Y. enterocolitica* and *Y. pseudotuberculosis* in serum or a tissue sample. Tissue samples contemplated can be rodents and human, or other mammals. Ancillary reagents would include standard anti-rodent or anti-human antibodies.

In another embodiment, the present invention relates to a vaccine for protection against *Y. pestis* infections by aerosol or subcutaneous route (insect bite). The vaccine comprises F1-V protein, or an immunogenic portion thereof, from a specific strain or species of *Yersinia pestis*. It could also contain V antigen from *Y. enterocolitica* and *Y. pseudotuberculosis*. The vaccine can be prepared by inducing expression of a recombinant expression vector comprising F1-V protein sequence and purifying the resulting protein. The purified F1-V protein is prepared for administration to mammals by methods known in the art, which can include filtering to sterilize the solution, diluting the solution, adding an adjuvant and stabilizing the solution. The vaccine can be lyophilized to produce a vaccine against *Y. pestis* in a dried form for ease in transportation and storage. Further, the vaccine may be prepared in the form of a mixed vaccine which contains the F1-V protein described above and at least one other antigen as long as the added antigen does not interfere with the effectiveness of the vaccine and the side effects and adverse reactions are not increased additively or synergistically.

The vaccine may be stored in a sealed vial, ampule or the like. The present vaccine can generally be administered in the form of a liquid or suspension. In the case where the vaccine is in a dried form, the vaccine is dissolved or suspended in sterilized distilled water before administration. Generally, the vaccine may be administered orally, subcutaneously, intradermally or intramuscularly but preferably intranasally in a dose effective for the production of neutralizing antibody and protection from infection or disease.

In another embodiment, the present invention relates to a method of reducing *Y. pestis* infection symptoms in a patient with bubonic or pneumonic plague by administering to said patient an effective amount of F1-V protein antibodies including those made in humans, either polyclonal or combinations of monoclonals to F1 and V antigen, as described above. When providing a patient with F1-V antibodies, the dosage administered will vary depending upon such factors as the patient's age, weight, height, sex, general medical condition, previous medical history, etc. In general, it is desirable to provide the recipient with a dosage of the above compounds which is in the range of from about 1 pg/kg to 500 mg/kg (body weight of patient), although a lower or higher dosage may be administered.

Described below are examples of the present invention which are provided only for illustrative purposes, and not to limit the scope of the present invention. In light of the present disclosure, numerous embodiments within the scope of the claims will be apparent to those of ordinary skill in the art.

The following Materials and Methods were used in the Examples below.

DNA methods. All restriction enzymes used were purchased from Life Technologies (Gaithersburg, Md.). Plasmid DNA samples were purified using a Qiagen plasmid purification kit (Qiagen, Inc., Chatsworth, Calif.) All oligonucleotide primers were synthesized on an Applied Biosystems model 391 DNA synthesizer (Foster City, Calif.) and the polymerase chain reaction (PCR) was performed using a DNA Thermal Cycler (Perkin-Elmer Cetus, Norwalk, Conn.). DNA sequencing was performed by the dideoxy-chain termination method [Sanger et al. (1977) Proc. Natl. Acad. Sci. 74: 5463-5467] using [$\alpha$-$^{35}$S]dATP (Amersham, Arlington Heights, Ill.). Genetic manipulations were performed by standard procedures [Sambrook et al. (1989) *Molecular Cloning: A Laboratory Manual*, 2nd Ed. Cold Spring Harbor Laboratory Press, Cold Spring Harbor, N.Y.].

Analytical methods. Protein content was determined by the bicinchoninic acid-Lowry method with BSA as a standard. (Pierce). Purified F1-V was analyzed by sodium dodecyl sulfate (SDS)-polyacrylamide gel electrophoresis (PAGE) on 10% tricine gels (Novex, San Diego, Calif.) and visualized by Coomassie blue R-250 (Bio-Rad Laboratories, Hercules, Calif.) staining.

EXAMPLE 1

Construction, Purification, and Characterization of Recombinant F1-V Fusion Protein.

To first isolate the F1 structural gene minus its stop codon, plasmid pYPR1 (kindly provided by T. Schwan, Rocky Mountain Laboratories, Hamilton, Mont.) containing the F1 operon [Simpson et al. (1990) *Am. J. Trop. Med. Hyg.* 43:389-396] was used as template DNA in a PCR using as the forward oligonucleotide primer, GGCGCGGCATATGAAAAAAATCAGTTCC (SEQ ID NO:3), containing an internal Nde I restriction site (underlined), and the reverse primer, CTCGAATTCTTGGTTAGATACGGT (SEQ ID NO:4), containing an internal Eco RI site (underlined). The V antigen gene was then isolated by PCR using plasmid DNA from a pigmentation negative derivative (Pgm$^-$) of *Y. pestis* CO92, the forward oligonucleotide primer, CGC GAATTCATGATTAGAGCCTACGAA (SEQ ID NO: 5), containing an internal Eco RI site (underlined), and the reverse primer, CGCGGATCCTCATTTACCAGACGTGTCA (SEQ ID NO:6) containing an internal Bam HI site (underlined).

The purified F1 PCR product was then digested with Nde I and Eco RI while the V antigen purified PCR product was digested with Eco RI and Bam HI. Both restricted fragments were then ligated to the Nde I and Bam H1 digested expression vector pET19b (Novagen, Madison, Wis.) and used to transform *Escherichia coli* strain BLR (Novagen) to create plasmid pF1V. The final protein contains an amino-terminal 10 histidines and enterokinase site from pET19b followed by the F1-V protein. The F1 portion consists of 170 amino acids followed by two amino acids, glutamic acid and phenylalanine (the Eco RI site) and the entire sequence of the V antigen. F1-V, therefore, has 521 amino acids with a predicted molecular mass of 57,926 daltons. The nucleotide sequence of the F1-V portion of pF1V was verified by sequencing. Two nucleotide differences were found between the V sequence present in F1-V and that reported previously for the V antigen [Price et al. (1989) *J. Bacteriol.* 171: 5646-5653]. A G was replaced by an A at base 247 of the open reading frame, resulting in a change from an alanine to a threonine. At base 324, a G was replaced with a C with no change in the amino acid at that site.

The F1-V fusion protein expressed from pET19b was isolated with 6 M urea as recommended (Novagen). Residual endotoxin was removed by passing F1-V over an endotoxin removing gel column (Pierce, Rockford, Ill.). After the column, F1-V contained 202 endotoxin units per mg of protein by Limulus amoebocyte lysate assay (Sigma, St. Louis, Mo.) (1 endotoxin unit=0.1 ng of *E. coli* 055:B5 LPS standard).

Figure 2:
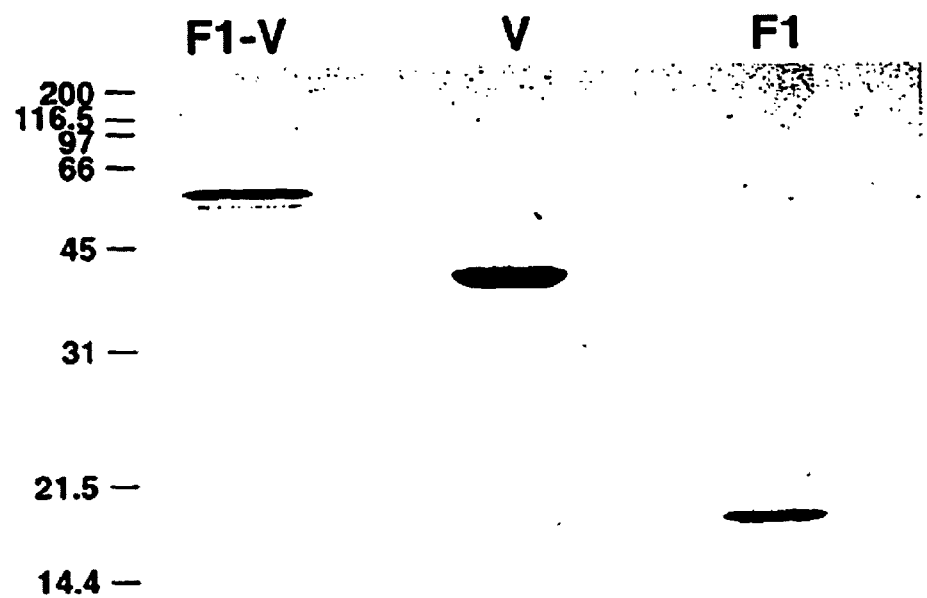
FIG. 2 shows the gel electrophoresis of F1-V fusion protein. The F1-V fusion protein expressed from pET19b was isolated with 6M urea as recommended (Novagen). Residual endotoxin was removed by passing F1-V over an endotoxin removing gel column (Pierce, Rockford, Ill.). After the column, F1-V contained 202 endotoxin units per mg of protein by Limulus amoebocyte lysate assay (Sigma, St. Louis, Mo.) (1 endotoxin unit=0.1 ng of *E. coli* O55:B5 LPS standard). Recombinant F1 and V were cloned separately and purified as described in Andrews et al. (1996) *Inf. Immun.* 64:2180-2187. F1-V, V and F1 proteins (2 μg each) were subjected to SDS-PAGE on 10% tricine gels (Novex, San Diego, Calif.) and visualized by Coomassie brilliant blue staining.

The recombinant F1-V fusion protein constructed in pET19b consists of the F1 protein fused at its carboxyl terminus to the amino terminus of the entire V antigen. F1-V had a relative molecular weight of 58,000 on SDS-PAGE (FIG. 2) which agreed with its predicted size of 57,926. The F1-V protein reacted on Western blot with both rabbit polyclonal antibody to F1 as well as mouse monoclonal antibodies directed against V antigen (data not shown). Recombinant F1 and V antigen are also shown in FIG. 2.

After establishing that F1-V had a relative molecular weight consistent with its DNA coding sequence and contained both F1 and V specific epitopes, we tested its ability to protect mice against plague.

EXAMPLE 2

Animal Immunization and Challenge with *Y. pestis*.

Groups of female 8-10 week old Swiss Webster (Hsd:ND4) mice (Harlan Sprague Dawley, Indianapolis, Ind.) were immunized subcutaneously on days 0 and 28 with 0.2 ml of the F1-V, F1, or V antigen preparation adsorbed to the aluminum hydroxide adjuvant, Alhydrogel (1.3%, Superfos Biosector, Vedbaek, Denmark, 0.19 mg aluminum per dose), the human whole-cell plague vaccine U.S. Pharmacopeia (USP) (Greer Laboratories, Lenoir, N.C.) or Alhydrogel alone as a control. Serum obtained on day 58 after initial immunization was assayed for anti-F1 and anti-V IgG antibody by standard ELISA on individual animals and group geometric mean titers determined. Titers were determined as the reciprocal of the maximum dilution giving an absorbance greater than 0.1 units after subtraction of nonspecific binding in normal serum.

The immunized animals were then challenged on day 78 by either the subcutaneous or aerosol route with wild-type $F1^+$ *Y. pestis*, CO92 (kindly provided by T. Quan, Center for Disease Control, Ft. Collins, Colo.) or C12, an $F1^-$ isogenic derivative of CO92 with a deletion in the F1 structural gene [Worsham et al. (1995) *Contrib. Microbiol. Immunol.* 13: 325-327]. The inocula for s.c. and aerosol challenge were prepared and the animals challenged by s.c. and aerosol routes as previously described [Welkos et al. (1995) *Contrib. Microbiol. Immunol.* 13: 299-305]. The s.c. $LD_{50}$ is 9.1 and 1.9 CFU for $F1^-$ C12 (37) and $F1^+$ CO92 (32) strains, respectively. The aerosol $LD_{50}$ is $1.1 \times 10^5$ and $2 \times 10^4$ CFU (32) for $F1^-$ C12 and $F1^+$ CO92 strains, respectively.

All animal experiments were conducted in accordance with the *Guide for the Care and Use of Laboratory Animals* (Committee on Care and Use of Laboratory Animals of the Institute of Laboratory Animal Resources, National Research Council. 1985. Guidelines for the care and use of laboratory animals revised. National Institutes of Health publication no. 86-23. National Institutes of Health, Bethesda, Md.) and animals were provided food and fresh water ad libitum during the experiment.

Efficacy of F1-V against Bubonic Plague.

In two separate experiments (Table 1), mice immunized with 13.6 μg of F1-V were protected (90-100% survival) against a subcutaneous challenge with a moderate (57 $LD_{50}$) or high ($1.1 \times 10^6$ $LD_{50}$) dose of the $F1^-$ *Y. pestis* strain, C12, while all control animals died. Another group of animals immunized with 27.2 μg of F1-V all survived (100%) the high-dose challenge. As expected, F1 alone, when adsorbed to Alhydrogel, did not protect animals against challenge with the $F1^-$ C12 strain. Animals given 10 μg of V were afforded the same degree of protection (90% survival) as with F1-V, against the high-dose challenge. Thus, the protective efficacy of the F1-V fusion protein against infection with an $F1^-$ *Y. pestis* strain was equivalent at this challenge dose, to that provided by V alone. In marked contrast, in a separate experiment, the current human, whole-cell plague vaccine USP, failed to protect against a low dose challenge; none of nine challenged animals survived.

TABLE 1

Efficacy of F1-V vaccination against a lethal subcutaneous *Y. pestis* infection of mice.

| Treatment Group | Strain | Challenge dose[a] | Survivors/ total |
|---|---|---|---|
| Alhydrogel alone | $F1^-$ C12 | 57 | 0/10 |
| 13.6 μg F1-V | " | 57 | 10/10 |
| 10 μg F1 | " | 60 | 0/10 |
| Plague USP[b] | " | 124 | 0/9 |
| Alhydrogel alone | " | $1.1 \times 10^6$ | 0/10 |
| 13.6 μg F1-V | " | $1.1 \times 10^6$ | 9/10 |
| 27.2 μg F1-V | " | $1.1 \times 10^6$ | 10/10 |
| 10 μg V | " | $1.1 \times 10^6$ | 9/10 |

[a]Number of $LD_{50}$
[b]The licensed, human, whole-cell plague vaccine.

Efficacy of F1-V against Pneumonic Plague.

We next determined the efficacy of F1-V against pneumonic plague induced by an aerosol challenge (Table 2). Mice immunized with 13.6 μg of F1-V were completely protected (100% survival) against a moderate (91 $LD_{50}$) or high (590 $LD_{50}$) aerosol dose of the $F1^-$ *Y. pestis* strain, C12. Animals given 27.2 μg of F1-V were also completely protected against the high-dose challenge. Similarly, V protected animals exposed to the high-dose aerosol challenge, with 80% of animals surviving. However, as with the s.c. challenge, the plague vaccine USP failed to protect against fatal pneumonic plague; none of eight challenged animals survived. Thus, the whole-cell plague vaccine USP failed to protect mice against challenge with the $F1^-$ strain by either the s.c. or aerosol route, while it does protect against s.c. challenge [Andrews et al. (1996) *Infect. Immun.* 64:2180-

2187; Simpson et al. (1990) *Am. J. Trop. Med. Hyg.* 43:389-396] and partially protects with prolongation of time to death against aerosol challenge with F1$^+$ strains [Andrews et al., ibid.; Pitt et al. (1994) Abstr. E-45. In: Abstracts of the 94th General Meeting of the American Society for Microbiology 1994. American Society for Microbiology, Washington, D.C.; Smith and Packman (1966) *Brit. J. Exp. Path.* 47: 25-34]. This differential protection against F1$^+$ and F1$^-$ strains and the absence of an immune response to V antigen in the plague vaccine USP group (Table 2) in agreement with other studies [Chen et al. (1961) *J. Immunol.* 87:64-71; Williamson et al. (1995) *FEMS Immunol. Med. Microbiol.* 12:223-230], strongly suggest that the major protective immunogen in the plague vaccine USP is F1 and that V antigen and other possible immunogens are absent.

The F1-V also protected (100% survival) against a high-dose aerosol challenge with the F1$^+$ *Y. pestis*, CO92 strain isolated from a fatal human pneumonic case. While these studies were in progress, a report described the increased effectiveness of co-immunization with F1 and V antigen in protecting against subcutaneous challenge with an F1$^+$ strain [Williamson et al., ibid.]. No studies were performed with F1$^-$ strains or against an aerosol challenge.

TABLE 2

Efficacy of F1-V vaccination against a lethal aerosol *Y. pestis* infection of mice

| Treatment Group | Strain | Challenge dose$^a$ | Survivors/ Total | Geometric mean antibody titer$^b$ | |
|---|---|---|---|---|---|
| | | | | F1 | V |
| Alhydrogel alone | F1$^-$C12 | 91 | 0/9 | NT$^c$ | NT |
| 13.6 µg F1-V | " | 91 | 10/10 | NT | NT |
| Alhydrogel alone | " | 590 | 0/14 | <640 | <640 |
| 13.6 µg F1-V | " | 590 | 10/10 | 66,540 | 432,376 |
| 27.2 µg F1-V | " | 590 | 10/10 | 108,094 | 432,376 |
| 10 µg V | " | 590 | 8/10 | NT | 655,360 |
| Plague USP$^d$ | " | 590 | 0/8 | 55,738 | <640 |
| Alhydrogel alone | F1$^+$CO92 | 761 | 1/10 | NT | NT |
| 13.6 µg F1-V | " | 761 | 10/10 | NT | NT |

$^a$Number of LD$_{50}$
$^b$Serum obtained on day 58 after the initial vaccine dose was assayed for anti-F1 and anti-V IgG antibody by ELISA on individual animals and group geometric mean titers determined as described in Materials and Methods.
$^c$Not tested.
$^d$The licensed, human, whole-cell plague vaccine.

Our results clearly demonstrate that mice immunized with a fusion protein, consisting of the F1 capsular antigen fused at its carboxyl terminus to the amino terminus of the V antigen of *Y. pestis*, were provided with excellent protection against both parenteral and aerosol challenge with an F1$^-$ *Y. pestis* strain. The F1-V fusion protein also protected mice against an aerosol challenge with an F1$^+$ *Y. pestis* strain. Other workers, as noted previously, showed that V antigen protects animals against challenge with virulent F1$^+$ strains, results which we have confirmed and extended to aerosol challenge. This raises the issue of whether the F1 portion of F1-V is immunogenic and contributes to the protection against challenge with the F1$^+$ *Y. pestis* strain CO92. Several lines of evidence suggest that the F1 portion is immunogenic and protective. The development of high levels of antibody to F1 after immunization with F1-V (Table 2) and the numerous reported studies showing a strong correlation between the level of antibody to F1 and protection against infection [Williams and Cavanaugh (1979) Bull. WHO 57:309-313] suggest the F1 portion of F1-V helps protect against challenge with F1$^+$ *Y. pestis*. Further support for a protective role for the F1 portion of F1-V was provided by our observations with a smaller F1-V fusion protein we constructed that consisted of the entire F1 gene fused at its carboxyl terminus to amino acids 168 to 275 of V antigen. This fusion protein was unable to effectively immunize mice against a subcutaneous challenge with the F1$^-$ *Y. pestis* C12 strain (3 survivors out of 10 mice challenged with 55 LD$_{50}$, data not shown), showing that the V segment of the fusion protein was not protective. However, this same fusion protein was able to protect mice against the F1$^+$ *Y. pestis* CO92 strain (10 survivors out of 10 mice challenged subcutaneously with 63 LD$_{50}$, data not shown). These results indicate the F1 portion of this fusion protein was immunogenic, enabling mice to survive challenge against infection with the F1$^+$ *Y. pestis* CO92, while the V segment failed to elicit a significant protective immune response against challenge with the V antigen expressing but F1$^-$ *Y. pestis* C12 strain. The value of a combined immune response to both F1 and V for combating infection with F1$^+$ *Y. pestis* strains is supported by the studies of Burrows and Bacon [Burrows, T. W. (1963) *Ergeb. Mikrobiol. Immunitatsforch. Exp. Ther.* 37:59-113; Burrows and Bacon (1958) *Brit. J. Exp. Pathol.* 39: 278-291] who found that serum from rabbits immunized with attenuated strains of *Y. pestis* expressing both F1 and V antigen provided better passive protection in mice against wild type F1$^+$ *Y. pestis* than serum from rabbits immunized with attenuated *Y. pestis* strains expressing only V antigen. It is also supported by the recent study showing increased protection by co-immunization of F1 with V antigen [Williamson et al., ibid.]. Better protection by antibody directed against both F1 and V might occur by counteracting both the anti-phagocytic activity associated with F1 [Burrows, T. W., ibid.] and the virulence-enhancing activity associated with secreted V antigen [Nakajima et al. (1995) *Infect. Immun.* 6 3: 3021-3029].

An additional advantage of a vaccine containing both F1 and V is that F1 should protect against variant strains of *Y. pestis* which might be altered in the amount or composition of V antigen, in a manner analogous to that by which V protects against F1$^-$ strains. Indeed, isolates deficient in V, determined immunologically, have been cultured from immunized animals infected with V-containing, wild-type *Y. pestis* [Williams et al. (1974) *Trans. Roy. Soc. Trop. Med. Hyg.* 68:171]. Furthermore, variability in the structural gene for V has been described for *Y. pseudotuberculosis* [Motin et al. (1994) *Infect. Immun.* 62:4192-4201], although to date, this has not been reported for *Y. pestis*.

Another potential advantage of an F1-V multicomponent vaccine would be to protect individuals who may be non-responders to one component of a vaccine. Indeed, some recipients of the current plague vaccine USP fail to develop an antibody response to F1 [Marshall et al. (1974) *J. Infect. Dis.* 129:S26-S29]. A similar approach to the development of recombinant multicomponent vaccines may be of value against other infectious diseases.

In summary, we constructed an F1-V fusion protein to provide optimal protective immunity against pneumonic as well as bubonic plague due to either wild-type F1$^+$ *Y. pestis* or fully virulent F1$^-$ *Y. pestis* strains which may occur naturally or may develop after infection of vaccinated individuals. The new vaccine was shown to be effective against both F1$^-$ as well as F1$^+$ *Y. pestis* strains. Most importantly, it prevented both fatal pneumonic as well as bubonic infection. This vaccine candidate may lead to the development of an improved human plague vaccine.

What is claimed is:

1. A composition comprising a purified fusion protein comprising all of F1 antigen of *Yersinia pestis*, with or without its signal sequence, fused to the amino terminus of all of V antigen of *Yersinia pestis* by a linker which consists of the following sequence -Glu-Phe-, wherein the purified fusion protein is reactive with antibodies against F1 antigen of *Yersinia pestis* and antibodies against V antigen of *Yersinia pestis* and is capable of eliciting a protective immune response against F1 positive and F1 negative *Yersinia pestis* strains.

2. The composition of claim 1, wherein the F1 antigen lacks its signal sequence.

3. The composition of claim 1, and further comprising a pharmaceutically acceptable excipient.

4. The composition of claim 1, and further comprising an adjuvant.

5. The composition of claim 1, and further comprising an additional antigen.

6. The composition of claim 1, wherein the purified fusion protein comprises all of F1 capsular antigen of *Yersinia pestis* and all of V antigen of *Yersinia pestis*.

7. The composition of claim 1, wherein a residual amount of endotoxin is removed.

8. A F1-V protein having the amino acid sequence specified in SEQ ID NO:2.

9. The composition of claim 5, wherein the additional antigen is a V antigen from *Yersinia pesudotuberculosis* or *Yersinia enterocolitica*.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 1566 bp
      (B) TYPE: Nucleic acid
      (C) STRANDEDNESS: Single
      (D) TOPOLOGY: Linear (xi) SEQUENCE DESCRIPTION: SEQ ID NO: 1:

```
ATGGGCCATC  ATCATCATCA  TCATCATCAT  CATCACAGCA               40
GCGGCCATAT  CGACGACGAC  GACAAGCATA  TGAAAAAAAT               80
CAGTTCCGTT  ATCGCCATTG  CATTATTTGG  AACTATTGCA              120
ACTGCTAATG  CGGCAGATTT  AACTGCAAGC  ACCACTGCAA              160
CGGCAACTCT  TGTTGAACCA  GCCCGCATCA  CTCTTACATA              200
TAAGGAAGGC  GCTCCAATTA  CAATTATGGA  CAATGGAAAC              240
ATCGATACAG  AATTACTTGT  TGGTACGCTT  ACTCTTGGCG              280
GCTATAAAAC  AGGAACCACT  AGCACATCTG  TTAACTTTAC              320
AGATGCCGCG  GGTGATCCCA  TGTACTTAAC  ATTTACTTCT              360
CAGGATGGAA  ATAACCACCA  ATTCACTACA  AAAGTGATTG              400
GCAAGGATTC  TAGAGATTTT  GATATCTCTC  CTAAGGTAAA              440
CGGTGAGAAC  CTTGTGGGGG  ATGACGTCGT  CTTGGCTACG              480
GGCAGCCAGG  ATTTCTTTGT  TCGCTCAATT  GGTTCCAAAG              520
GCGGTAAACT  TGCAGCAGGT  AAATACACTG  ATGCTGTAAC              560
CGTAACCGTA  TCTAACCAAG  AATTCATGAT  TAGAGCCTAC              600
GAACAAAACC  CACAACATTT  TATTGAGGAT  CTAGAAAAAG              640
TTAGGGTGGA  ACAACTTACT  GGTCATGGTT  CTTCAGTTTT              680
AGAAGAATTG  GTTCAGTTAG  TCAAAGATAA  AAATATAGAT              720
ATTTCCATTA  AATATGATCC  CAGAAAAGAT  TCGGAGGTTT              760
TTGCCAATAG  AGTAATTACT  GATGATATCG  AATTGCTCAA              800
GAAAATCCTA  GCTTATTTTC  TACCCGAGGA  TACCATTCTT              840
AAAGGCGGTC  ATTATGACAA  CCAACTGCAA  AATGGCATCA              880
AGCGAGTAAA  AGAGTTCCTT  GAATCATCGC  CGAATACACA              920
ATGGGAATTG  CGGGCGTTCA  TGGCAGTAAT  GCATTTCTCT              960
TTAACCGCCG  ATCGTATCGA  TGATGATATT  TTGAAAGTGA             1000
TTGTTGATTC  AATGAATCAT  CATGGTGATG  CCCGTAGCAA             1040
GTTGCGTGAA  GAATTAGCTG  AGCTTACCGC  CGAATTAAAG             1080
ATTTATTCAG  TTATTCAAGC  CGAAATTAAT  AAGCATCTGT             1120
CTAGTAGTGG  CACCATAAAT  ATCCATGATA  AATCCATTAA             1160
TCTCATGGAT  AAAAATTTAT  ATGGTTATAC  AGATGAAGAG             1200
ATTTTTAAAG  CCAGCGCAGA  GTACAAAATT  CTCGAGAAAA             1240
```

```
TGCCTCAAAC  CACCATTCAG  GTGGATGGGA  GCGAGAAAAA                    1280

AATAGTCTCG  ATAAAGGACT  TTCTTGGAAG  TGAGAATAAA                    1320

AGAACCGGGG  CGTTGGGTAA  TCTGAAAAAC  TCATACTCTT                    1360

ATAATAAGA   TAATAATGAA  TTATCTCACT  TTGCCACCAC                    1400

CTGCTCGGAT  AAGTCCAGGC  CGCTCAACGA  CTTGGTTAGC                    1440

CAAAAACAA   CTCAGCTGTC  TGATATTACA  TCACGTTTTA                    1480

ATTCAGCTAT  TGAAGCACTG  AACCGTTTCA  TTCAGAAATA                    1520

TGATTCAGTG  ATGCAACGTC  TGCTAGATGA  CACGTCTGGT                    1560

AAATGA                                                            1566

(2) INFORMATION FOR SEQ ID NO: 2:

(i) SEQUENCE CHARACTERISTICS:
        (A) LENGTH: 521
        (B) TYPE: Amino acid
        (C) STRANDEDNESS: Single
        (D) TOPOLOGY: Linear (xi) SEQUENCE DESCRIPTION: SEQ ID NO: 2:

Met Gly His His His His His His His His Ser Ser Gly
1               5                   10                  15

His Ile Asp Asp Asp Asp Lys His Met Lys Lys Ile Ser Ser Val
                20                  25                  30

Ile Ala Ile Ala Leu Phe Gly Thr Ile Ala Thr Ala Asn Ala Ala
                35                  40                  45

Asp Leu Thr Ala Ser Thr Thr Ala Thr Ala Thr Leu Val Glu Pro
                50                  55                  60

Ala Arg Ile Thr Leu Thr Tyr Lys Glu Gly Ala Pro Ile Thr Ile
                65                  70                  75

Met Asp Asn Gly Asn Ile Asp Thr Glu Leu Leu Val Gly Thr Leu
                80                  85                  90

Thr Leu Gly Gly Tyr Lys Thr Gly Thr Thr Ser Thr Ser Val Asn
                95                  100                 105

Phe Thr Asp Ala Ala Gly Asp Pro Met Tyr Leu Thr Phe Thr Ser
                110                 115                 120

Gln Asp Gly Asn Asn His Gln Phe Thr Thr Lys Val Ile Gly Lys
                125                 130                 135

Asp Ser Arg Asp Phe Asp Ile Ser Pro Lys Val Asn Gly Glu Asn
                140                 145                 150

Leu Val Gly Asp Asp Val Val Leu Ala Thr Gly Ser Gln Asp Phe
                155                 160                 165

Phe Val Arg Ser Ile Gly Ser Lys Gly Gly Lys Leu Ala Ala Gly
                170                 175                 180

Lys Tyr Thr Asp Ala Val Thr Val Thr Val Ser Asn Gln Glu Phe
                185                 190                 195

Met Ile Arg Ala Tyr Glu Gln Asn Pro Gln His Phe Ile Glu Asp
                200                 205                 210

Leu Glu Lys Val Arg Val Glu Gln Leu Thr Gly His Gly Ser Ser
                215                 220                 225

Val Leu Glu Glu Leu Val Gln Leu Val Lys Asp Lys Asn Ile Asp
                230                 235                 240

Ile Ser Ile Lys Tyr Asp Pro Arg Lys Asp Ser Glu Val Phe Ala
                245                 250                 255
```

-continued

```
Asn Arg Val Ile Thr Asp Asp Ile Glu Leu Leu Lys Lys Ile Leu
             260                 265                 270

Ala Tyr Phe Leu Pro Glu Asp Thr Ile Leu Lys Gly Gly His Tyr
         275                 280                 285

Asp Asn Gln Leu Gln Asn Gly Ile Lys Arg Val Lys Glu Phe Leu
         290                 295                 300

Glu Ser Ser Pro Asn Thr Gln Trp Glu Leu Arg Ala Phe Met Ala
         305                 310                 315

Val Met His Phe Ser Leu Thr Ala Asp Arg Ile Asp Asp Asp Ile
         320                 325                 330

Leu Lys Val Ile Val Asp Ser Met Asn His Gly Asp Ala Arg
         335                 340                 345

Ser Lys Leu Arg Glu Glu Leu Ala Glu Leu Thr Ala Glu Leu Lys
         350                 355                 360

Ile Tyr Ser Val Ile Gln Ala Glu Ile Asn Lys His Leu Ser Ser
         365                 370                 375

Ser Gly Thr Ile Asn Ile His Asp Lys Ser Ile Asn Leu Met Asp
         380                 385                 390

Lys Asn Leu Tyr Gly Tyr Thr Asp Glu Glu Ile Phe Lys Ala Ser
         395                 400                 405

Ala Glu Tyr Lys Ile Leu Glu Lys Met Pro Gln Thr Thr Ile Gln
         410                 415                 420

Val Asp Gly Ser Glu Lys Lys Ile Val Ser Ile Lys Asp Phe Leu
         425                 430                 435

Gly Ser Glu Asn Lys Arg Thr Gly Ala Leu Gly Asn Leu Lys Asn
         440                 445                 450

Ser Tyr Ser Tyr Asn Lys Asp Asn Asn Glu Leu Ser His Phe Ala
         455                 460                 465

Thr Thr Cys Ser Asp Lys Ser Arg Pro Leu Asn Asp Leu Val Ser
         470                 475                 480

Gln Lys Thr Thr Gln Leu Ser Asp Ile Thr Ser Arg Phe Asn Ser
         485                 490                 495

Ala Ile Glu Ala Leu Asn Arg Phe Ile Gln Lys Tyr Asp Ser Val
         500                 505                 510

Met Gln Arg Leu Leu Asp Asp Thr Ser Gly Lys
         515                 520
```

(2) INFORMATION FOR SEQ ID NO: 3:

(i) SEQUENCE CHARACTERISTICS:
        (A) LENGTH: 28 bp
        (B) TYPE: Nucleic acid
        (C) STRANDEDNESS: Single
        (D) TOPOLOGY: Linear (xi) SEQUENCE DESCRIPTION: SEQ ID NO: 3:

GGCGCGGCAT ATGAAAAAAA TCAGTTCC                          28

(2) INFORMATION FOR SEQ ID NO: 4:

(i) SEQUENCE CHARACTERISTICS:
        (A) LENGTH: 24 bp
        (B) TYPE: Nucleic acid
        (C) STRANDEDNESS: Single
        (D) TOPOLOGY: Linear (xi) SEQUENCE DESCRIPTION: SEQ ID NO: 4:

CTCGAATTCT TGGTTAGATA CGGT                            24

```
(2) INFORMATION FOR SEQ ID NO: 5:

(i) SEQUENCE CHARACTERISTICS:
        (A) LENGTH: 27 bp
        (B) TYPE: Nucleic acid
        (C) STRANDEDNESS: Single
        (D) TOPOLOGY: Linear (xi) SEQUENCE DESCRIPTION: SEQ ID NO: 5:

CGCGAATTCA  TGATTAGAGC  CTACGAA                                             27

(2) INFORMATION FOR SEQ ID NO: 6:

(i) SEQUENCE CHARACTERISTICS:
        (A) LENGTH: 28 bp
        (B) TYPE: Nucleic acid
        (C) STRANDEDNESS: Single
        (D) TOPOLOGY: Linear (xi) SEQUENCE DESCRIPTION: SEQ ID NO: 6:

CGCGGATCCT  CATTTACCAG  ACGTGTCA                                            28
```